US00PP08998P

United States Patent [19]

Hope

[11] Patent Number: Plant 8,998

[45] Date of Patent: Nov. 29, 1994

[54] KALANCHOE PLANT NAMED TICO DARK ORANGE

[75] Inventor: Claude Hope, Cartago, Costa Rica

[73] Assignee: Ball Seed Company, West Chicago, Ill.

[21] Appl. No.: 183,384

[22] Filed: Jan. 18, 1994

[51] Int. Cl.[5] ..... A01H 5/00
[52] U.S. Cl. ..... Plt./87.15
[58] Field of Search ..... Plt. 87.15

*Primary Examiner*—James R. Feyrer
*Attorney, Agent, or Firm*—Foley & Lardner

[57] ABSTRACT

A new and distinct cultivar of Kalanchoe plant named Tico Dark Orange, characterized by its compact growth habit, dark orange flower color, freely branching habit which does not require pinching, peduncles which do not stretch during flowering or postproduction, excellent keeping quality, and its non-fading flowers and foliage.

1 Drawing Sheet

The present invention relates to a new and distinctive cultivar of Kalanchoe plant, botanically known as *Kalanchoe blossfeldiana,* and referred to by the cultivar name Tico Dark Orange.

The new cultivar was referred to during the breeding and selection process by the designation KAL 194 and is a product of a planned breeding program carried out by the inventor in Cartago, Costa Rica.

The new cultivar was originated from a cross made by the inventor in a controlled breeding program in Cartago, Costa Rica. The female or seed parent was the cultivar Linda Vista #1705-1. The male or pollen parent was the cultivar designated Linda Vista #1808-4. Both parents are proprietary cultivars used in the breeding program.

Tico Dark Orange was discovered and selected by the inventor as a flowering plant within the progeny of the stated cross in a controlled environment in Cartago, Costa Rica. Asexual reproduction of the new cultivar by terminal cuttings, as performed by the inventor at Cartago, Costa Rica, and subsequently performed at West Chicago, Ill., has demonstrated that the combination of characteristics as herein disclosed for the new cultivar are firmly fixed and are retained through successive generations of asexual reproduction.

Tico Dark Orange has not been observed under all possible environmental conditions. The phenotype may vary somewhat with variations in environment such as temperature, light intensity and daylength, without, however, any variance in genotype. The following observations, measurements and values describe the new cultivar as grown in West Chicago, Ill., under glass-covered greenhouse conditions which closely approximate those generally used in commercial practice. Values represent the average of six specimen plants observed.

The following traits have been repeatedly observed and are determined to be basic characteristics of Tico Dark Orange, which in combination distinguish this Kalanchoe as a new and distinct cultivar:

1. Dark orange flower color.
2. A more compact growth habit, with growth retardants not being required for growth regulation.
3. A freely branching habit which does not require pinching.
4. Relatively small leaves, with leaf size being proportional to plant size.

5. Peduncles which do not stretch during flowering or during postproduction.
6. Excellent keeping quality. Flowers do not fade and foliage maintains good color for up to seven weeks under office or home conditions.

The accompanying color photographic drawing is a top perspective view showing a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken at West Chicago, Ill.

Classification: *Kalanchoe blossfeldiana,* cv Tico Dark Orange.

Parentage:
- *Male parent.*—Linda Vista #1808-4.
- *Female parent.*—Linda Vista #1705-1.

Propagation: The new cultivar holds its distinguishing characteristics through successive propagations.
- A. *Type cutting.*—Terminal.
- B. *Time to root.*—7 days at 25° C.
- C. *Rooting habit.*—Fine, fibrous, well-branched.

Plant description:
- A. *Form.*—Upright and compact.
- B. *Habit of growth.*—Freely branching.
- C. *Foliage description.*—1. Size: Length approximately 8 cm, width 4 cm. 2. Shape: Ovate. 3. Texture: Succulent. 4. Margin: Serrated. 5. Color: Young foliage, top side is 147A, under side is 147A; mature foliage, top side is 147A, under side is 147A.

Flowering description:
- A. *Flowering habit.*—Freely flowering, panicles, cymose.
- B. *Natural flowering season.*—Autumn/winter in Northern Hemisphere. Flowering initiation and development can be induced under short day/-long night conditions.
- C. *Flower buds.*—Typical for cultivars of this type.
- D. *Flowers borne.*—Arising from leaf axils, above foliage.
- E. *Quantity of flowers.*—40 to 60 per cyme.

F. *Petals.*—1. Shape: Oblong/linear, tip acute. 2. Color: Top side when opening is 44A; mature top side is 43A with little fading; mature underside is also 43A. 3. Size of petals: 1.5 cm in length and 1.5 cm in width.

G. *Reproductive organs.*—1. Stamens: Eight (8) in number. a. Anther color: 149B. b. Pollen color: 6A. 2. Pistils: a. Stigma color: 14A. b. Style color: 149B. C. Ovaries: Four (4) in number, size 4 mm by 1 mm, color 149B.

Disease resistance: No fungal, bacterial or viral diseases have been observed to date.

It is claimed:

1. A new and distinct Kalancho plant named Tico Dark Orange, as described and illustrated.

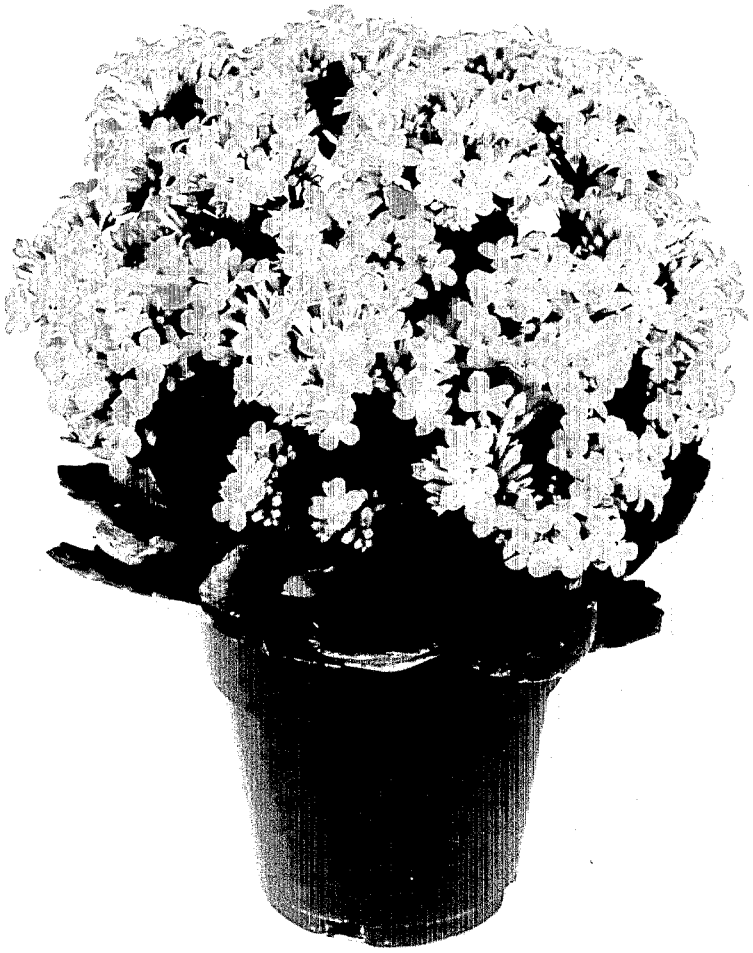

* * * * *